United States Patent [19]
Harper

[11] Patent Number: 6,027,937
[45] Date of Patent: Feb. 22, 2000

[54] METHOD FOR PROPAGATION OF INSECTA GERM CELLS

[76] Inventor: William Harper, 16541 Redmond Way #140C, Redmond, Wash. 98052

[21] Appl. No.: 09/134,964

[22] Filed: Aug. 18, 1998

[51] Int. Cl.⁷ ..................................................... C12N 5/06
[52] U.S. Cl. ........................ 435/348; 435/374; 435/383; 435/384; 435/387; 435/404; 435/405; 435/406
[58] Field of Search ..................................... 435/374, 383, 435/384, 387, 404, 405, 406, 348

[56] References Cited

U.S. PATENT DOCUMENTS

| | | | |
|---|---|---|---|
| 5,166,065 | 11/1992 | Williams et al. | 435/240.1 |
| 5,340,740 | 8/1994 | Petitte et al. | 435/240.2 |
| 5,453,357 | 9/1995 | Hogan | 435/7.21 |
| 5,656,479 | 8/1997 | Petitte et al. | 435/349 |
| 5,670,372 | 9/1997 | Hogan | 435/240.2 |

FOREIGN PATENT DOCUMENTS

| | | |
|---|---|---|
| 0834556 | 4/1998 | European Pat. Off. . |
| WO 95/21911 | 8/1995 | WIPO . |

OTHER PUBLICATIONS

Allis, C.D. et al., Dev. B10., 69, 451–465 (1979) "Pole Cells of Drosophilla Melanogaster in Culture".
Liebrich, W., Hist. Phil. Life Sci., vol. 15(1), pp. 33–44 (original and translation), 1993.
Jian, W. et al., Acta Entomological Sinica, vol. 37(1), pp. 1–6 (original and translation), Feb. 1994.
Sadrud–Din, S.Y. et al., Invertebrate Reproduction and Development, vol. 26(3), pp. 197–204, Dec. 1994.
Loeb, M.J. et al., J. Insect Physiol., vol. 42(11–12), pp. 1103–1111, 1996.
Okada, M., Protein, Nucleic Acid, and Enzyme, vol. 24(12), pp. 42–49, 1979.
Mahowald, A.P. et al., Symp. Soc. Dev. Biol., vol. 39, pp. 127–146, 1979.
Gonczy, P. et al., Development, vol. 124(21), pp. 4361–4371, Nov. 1997.
Chou, T.B. et al., Genetics, vol. 131, pp. 643–653, Jul. 1992.
Baikova, N.A. et al., Ontogenez, vol. 24(2), pp. 33–42 (original and translation), 1993.
Jordan, P. et al., J. of Cell Biology, vol. 139(7), pp. 1805–1819, Dec. 1997.
Sadrud–Din, S. et al., In Vitro Cellular and Developmental Biology Animal, vol. 30A (3 pt. 2), pp. 106, abstract # V–1042, Jun. 1996.
Sadrud–Din, S. et al., J. of Experimental Biology, vol. 199(2), pp. 319–325, 1996.
Sigma BioSciences Cell Culture Catalogue and Price List, pp. 56, 57, 61, 63, 170, 176, 179, and 180, 1996.
DeFrancesco, L., The Scientist, vol. 12(13), pp. 20–22, Jun. 1998.
Beeman, S.L. et al., J. Morph., vol. 152(2), pp. 177–220, 1977.
Scott, M.P. et al., Biochem., vol. 18(8), pp. 1588–1594, 1979.
Zhou, J.H. et al., J. Vet. Med., vol. 58(2), pp. 173–175, 1996.
Went, D.F., In Vitro, vol. 13(2), pp. 76–84, Feb. 1977.
Jaglarz, M.K. et al., Development, vol. 121(11), pp. 3495–3503, 1995.
Loeb, M.J. et al., In Vitro—Cellular and Development Biology, vol. 34(3 part 2), pp. 41–A abstract, Mar. 1998.
Buning, J., Wilhelm Roux's Archives of Dev. Biol, vol. 188(3), pp. 215–224, 1980.
Sadrud–Din, S.Y. et al., Invertebrate Reproduction & Development, vol. 26(3), pp. 197–204, Dec. 1994.
Dolci. S. et al.; Requirement for Mast Cell Growth Factor for Primordial Germ Cell Survival in Culture; Nature, 352: 809–811 (1991).
Dolci, S. et al,; Combined Action of Stem Cell Factor, Leukemia Inhibitory Factor. and cAMP on In Vitro Proliferation of Mouse Primordial Germ Cells; Molecular Reproduction and Development, 35: 134–139 (1993).
Evans, M. et al; Establishment in Culture of Pluripotential Cells from Mouse Embryos; Nature. 292: 154–165 (1981).
Godin, I. et al., Effects of the Steel Gene Product on Mouse Primordial Germ Cells In Culture; Nature, 352: 807–809 (1991).
Margolis, J. and A. Spradling; Identification and Behavior of Epithelial Stem Cells in the Drosophila Ovary; Development, 121: 3797–3807 (1995).
Matsui, A. et al.; Derivation of Pluripotential Embryonic Stem Cells from Murine Primordial Germ Cells in Culture; Cell. 70:841–847 (1992).
Matsui, A. et al.; Effect of Steel Factor and Leukemia Inhibitory Factor on Murine Primordial Germ Cells in Culture; Nature, 353: 750–752 (1991).
Piedrahita, J. et al.; Generation of Transgenic Porcine Chimeras Using Primordial Germ Cell Derived Colonies; Biology of Reproduction. 58(5): 1321–1329 (1998).
Potten, C. and M. Loeffler; Stem Cells: Attributes, cycles, spirals, pitfalls and Uncertainties—Lessons from the Crypt: Development, 110: 1001–1020 (1990).
Resnick, J. et al. ; Long–term Proliferation of Mouse Primordial Germ Cells in Culture; Nature, 359: 550–551 (1992).
Shim, H. et al.; Isolation of Pluripotential Stem Cells from Cultured Porcine Primordial Germ Cells; Biology of Reproduction, 57(5): 1089–1095 (1997).
Smith, A. and M. Hooper; Buffalo Rat Liver Cells Produce a Diffusible Activity Activity which Inhibits the Differentiation of Murine Embryonal Carcinoma And Embryonic Stem Cells; Developmental Biology, 121: 1–9 (1987).
Whitefleet–Smith, J. et al.; Expression of Human Plasminogen cDNA in a Baculovirus Vector–Infection Insect Cell System : Arch. Biochem. and Biophs., 271: 390–399 (1989).

*Primary Examiner*—Jean C. Witz
*Attorney, Agent, or Firm*—Townsend and Townsend and Crew

[57] ABSTRACT

A method is disclosed for the in vitro growth and proliferation of germ cells obtained from the ovarioles of an insect. By culturing these cells in a medium supplemented with soluble cytokines and mitogenic agents and independent of feeder-cells, they can be induced to proliferate. Cells are stored by cryogenic means for future use.

12 Claims, No Drawings

METHOD FOR PROPAGATION OF INSECTA GERM CELLS

BACKGROUND OF THE INVENTION

1. Field of the Invention

This invention discloses a novel method for the in vitro culture and proliferation of Insecta germ cells by the application of soluble cytokinic and mitogenic agents.

2. Background Art

All insect cells were once thought to be impossible to culture, fully half a century passed between the first successful mammal cell cultures and 1962 when Grace finally formulated a medium capable of supporting insect cells in vitro. Even today investigations of insects cells lags far behind. Mice, humans, pigs, and birds receive the vast share of research attention. Only with the baculovirus expression system have a select number of insect tissue cells found a significant role as minute disposable factories for producing invaluable medical and other proteins. Large numbers of these tissue cells have been established in collections to support this particular system in its various forms. Notably absent from these tissues collections are any insect cells cultures or lines derived from germ cells. All germ cell cultures have proven very difficult to culture and successfully propagate; only murine (mouse). avian (chicken) and porcine (pig) embryos have yielded sustained germ cell cultures that have been reported in the literature. (Margolis J. and A. Spradling, 1995. *Development* 121:3797–3807: Potten, C. and M. Loeffler, 1990. *Development* 110:1001–1020).

In contrast to the complete lack of success in culturing insect germ cells, the 1980's first saw murine germ cells cultured with limited success on mouse fibroblast and buffalo rat liver cells. This early work was soon followed in the early 1990's by complete success reported by several teams in diverse locations within a matter of months of each other. Petitte was the first to achieve an avian (chicken) germ cell culture in the same period. Advances in murine and avian germ cell culture were made possible by a new array of compounds that demonstrated enhanced survival and growth characteristics when applied to primordial germ cells. Dolci, Matsui, Godin, Resnick and Hogan all reported various results culturing murine germ cells with several mediums and feeder layers supplemented with diverse materials typically including stem cell factor, leukemia inhibitory factor, and fibroblast factors in combination with numerous other agents and techniques. (Evans, M. et al., 1981. *Nature* 292:154: Smith, A. et al., 1987, *Developmental Biology* 121:1–9: Petitte, U.S. Pat. No. 5,340,740(1994): Petitte, U.S. Pat. No. 5,656,479(1997): Dolci, S. et al., 1991, *Nature* 352:809–811: Dolci, S. etal., 1993, *Molecular Repro. Dev.* 35: 134–139: Matstui, Y. etal., 1991. *Nature* 353:750–752: Godin. I. et al., 1991. *Nature* 352:807–809: Williams, U.S. Pat. No. 5,166,065 (1992Resnick. J. et al., 1992. *Nature* 359:550–551: Hogan, U.S. Pat. No. 5,453,357 (1995). Progress slowed following this burst of achievement, little use and no advancement of germ cell culturing methods has been reported for murine and avian cultures since. After a lapse of six more years Shim and Piedrahita reported independently in late 1997 and early 1998 that porcine embryonic germ cells had been successfully cultured. (Shim. H. et al., 1997. *Biology of Reproduction* 57 (5): 1089–1095: Piedrahita. J. et al., 1998, *Biology of Reproduction* 58 (5): 1321–1329).

While success has been reported for murine, avian and porcine germ cell cultures there are no reports of success establishing a method for insect germ cells culturing: the pattern of slow progress for insect cell research established in the first half of the century is repeating itself. There are reasons for this delay. Insect cells are distinctly different from other animal cell and comparatively little is known about insect cell metabolism and beyond observational data equally little is known about influencing or culturing their germ cells. There is a relatively small body of literature on the subject. Insect and vertebrate animals are classified in totally different phylogenetic systems. Insect cells developed in a substantially older and distinctly more primitive evolutionary period than that experienced much later by avians and most recently by modem mammals. Insects have a radically dissimilar and unique life cycle resulting from distinct cellular properties. Basically, insect cells often react in different and unanticipated ways when techniques and materials developed for a few select vertebrates are applied to them.

The best known example of how insect cells are fundamentally different from mammal cells is the basis of the baculovirus expression system. Early investigators tried repeatedly to extract recombinant intact human plasminogen from a number of different cell types and each attempt failed. (Whitefleet-Smith, J. et al., 1989, *Arch. Biochem. Biophs.* 271:390–399). One known unique cellular property inherent to insect cells is the lack of intracellular plasminogen activators, a feature found in mammals. Mammal cells with activators rapidly convert plasminogen to plasmin before the material can be recovered and consequently make an expression system based on mammal cells essentially useless. Insect cells, lacking these activators, can create and maintain significant amounts of recombinant human plasminogen with relative efficiency before lysis. Insect cells have many radically distinct characteristics, known and mostly unknown, which absolutely preclude any confident assumption about transferring knowledge learned from manuals to conclusions concerning insects.

The culture requirements of insect cells further illustrate these differences. In culture insect cells have a greater oxygen uptake rate than mammalian cells. The insect cell's membranes are comparatively fragile. surfactants are needed to protect and strength the membranes against the minute hydrodynamic forces of most cultivating systems. Insect cells grow optimally at about 27° C., mammals prefer closer to 37° C. Media for culturing insect cells needs to be set at a 6.2 pH, mammalian cell require a 7.4 pH. Most insect germ cells never mature but instead become a nutritive attachment to those cells that do become oogonia; there is simply no equivalent system in the formation of mammalian or avian germ cells. These few illustrative facts indicate the scope of the dissimilarities between the cells of most animal insect cells, and specifically insect germ cells.

SUMMARY OF THE INVENTION

The object of the present invention is to develop a method for the substantial proliferation of viable. undifferentiated insect germ cells.

It is still further an object of the present invention to provide clonal cultures of insect germ cells and their progeny in an in vitro feeder-cell independent culture.

It is still further an object of the present invention to create a method for insect germ cell proliferation that will contribute to a system for the economic mass-production of pollinating and other forms of beneficial insects. Specifically, pollinating insects that fertilize entomophilous plants capable of bearing a crop.

It is still further an object of the present invention to create a method whereby substantial numbers of insect germ cells are available for large-scale storage by cryogenic freezing so that genetic resources can be preserved and on-demand resuscitation can be performed.

It is still further an object of the present invention to create a method whereby one or more genetically modified germ cells altered by genetic engineering techniques can be naturally replicated and thereby achieve sufficient numbers to permit a substantial clonal harvest of commercial value substantially based on the desirability of the introduced genetic trait or traits.

These and other objects will become more apparent from the following description of the present invention which describes a method for preparing an in vitro insect germ call culture system comprising the proper preparation of an appropriate chemically defined culture medium containing at least one soluble cytokine compound and at least one mitogenic compound and added undifferentiated insect germ cells. For the purposes of the present invention, the terms "primordial germ cells", "terminal filament germ cells", "pole cells", "germ stem cells", "embryonic germ stem cell", "cystoblast", "oogonia", "terminal filament cells", "tapetum cells", and all other terms indicating undifferentiated insect germ cells capable of replicating by mitosis regardless of their point of origin in an insect's life cycle are encompassed by the terms "germ cell" and "germ cells".

Germ cells are cultured in vitro in fortified serum-free culture media containing soluble differentiating-inhibiting cytokinic and proliferation inducing mitogenic agents and respond by proliferating through mitogenic division. By maintaining a 50% confluency limit in the culture to determine passage points and frequent medium exchanges to remove organic waste and introduce oxygen, reproductive growth is maintained through twenty germ cell population doublings. Utilizing a liquid-only culture environment the need for a feeder-cell layer is eliminated and many unexpected benefits resulted. The basis for these benefits once again lies in physiological distinctions that exist between mammal and insect ovaries at the cellular level. Insect germ cells are held loosely in the tropharium region of the insect's ovarioles, an area immediate to the terminal filament. Insect germ cells are neither attached nor implanted in the associated follicular tissue constituting the ovarial sac, but rather are contained in a manner similar to freely moving marbles held within a sock. In contrast germ cells in mammals are attached in ovarian support tissue functionally replicated by the use feeder-cell layer; avian germ cells embed in the feeder-cell layer. The elimination of feeder-cells as a culture requirement from this invention provides benefits in terms of economy, control, efficiency and simplicity.

All previous germ cell cultures have been achieved with murine, avian and porcine cells, and all these germ cell cultures have employed feeder-cell layers to achieve their results. Hogan specifically discloses a feeder-cell produced "membrane associated steel factor" in every claim element (Hogan, U.S. Pat. Nos. 5,453,357 and 5,670,372). Petitte similarly employs a mouse fibroblast as the preferred embodiment and further contemplates feeder layers composed of cells from other mammalian species (Petitte, U.S. Pat. Nos. 5,340,740 and 5,656,479). Shim cultured porcine embryonic germ cells on mitotically inactivated murine fibroblast feeder-cells and Piedrahita plated porcine primordial germ cells on STO feeder-cells (Shim, H. et al., 1997, *Biology of Reproduction* 57 (5): 1089–1095: Piedrahita, J. et al., 1998. *Biology of Reproduction* 58 (5): 1321–1329).

The distinct histology of the insect's ovariole gives rise to the unique means of germ cell culture contemplated by this invention. Evolutionarily habituated to a fluid environment and without a need to attach, the insect germ cells do not require the prerequisite feeder-cell layer as currently practiced in the art Insect germ cells cultured by the process of this invention produce with unexpected ease a culture by mitogenic proliferation.

DETAILED DESCRIPTION OF THE INVENTION

The terms "insect" and "Insecta" or grammatical equivalents refers to any and all living organisms that are classified as members of the Insecta class, including but not limited to such insects as found in the orders of Diptera, Hemiptera, Hymenoptera, Lepidoptera, Orthoptera, etc. Specifically included in these terms are new species and subspecies identifiable by accepted taxametric classification as may be discovered or created.

The term "feeder-cell independent culture" or grammatical equivalents means the growth of cells in vitro in the absence of a layer of different cells which generally are first plated upon a culture dish to which cells of interest are added. The feeder-cells provide a substratum for the attachment of the cells of interest and additionally serve as a source for cytokinic, mitogenic and survival factors. Feeder-cell independent cultures herein utilize chemically defined cytokinic, mitogenic and other survival factors as provided by supplementation of the liquid culture medium with either purified factors or factor extracts from other cells. Thus, in feeder-cell independent cultures, the cells in the culture dish are primarily cells of interest and do not contain other cell types required to support the growth of the cells of interest.

The term "sustained" as used herein with respect to cells and cell culture refers to a cell or cell culture capable of undergoing further cell division, even if the cells are eventually subject to senescence.

The present invention is explained in greater detail in the following non-limiting Examples expressed as simple protocols presented as preferred embodiments.

EXAMPLE 1
Preparation of Insecta Germ Cells

The cells utilized in the method of this invention may be obtained from the ovarian tissues of solitary bees breaking diapause (Hymenoptera, Osmia sps.) by harvesting whole polytrophic mesoistic ovaries from the bodies of decapitated females. Start by repeatedly flushing the exterior body with disinfecting solutions. Under magnification, with sterile working field and tools, the body of the fixed insect is opened and the ovarian tract removed to a petri dish containing Hank's Balanced Saline Solution (HBSS) at room temperature. Repeatedly wash the organ with fresh exchanges of HBSS to clean the organ of body fluids. fungi, bacteria, loose extraneous materials, and similar sources of possible contamination. Move the cleansed ovarian tract to a sterile petri dish containing sterile HBSS, place the dish in a decontaminated laminar flow cabinet equipped with HEPA filters and setup to facilitate use of a dissecting microscope. Layout the ovary along its longest dimension note the location of the ovarioles with specific attention to the placement of the terminal filament and immediate most anterior zone of the germarial region. With precision severe the tropharium (or most anterior third of the germinal region depending on insect) from the ovariole under HBSS to prevent germ cell damage. Remove ovary tissue from the work area when finished harvesting the terminal filament segments from the ovarioles. Avoiding cuts and crushing, rip open the tropharium and terminal filament sheath exposing the germ cells within. The germ cells are identifiable by their rounder appearance, smooth cellular surface, colorlessness and have a discernible shiny appearance in appropriate lighting. Separate somatic follicular cells from the germ cells by cautious fine needle and pipette currents. By repeated gentle pipetting of HBSS containing cellular material so as to separate materials. 4–8 viable germ cells per segment may be separated, identified, selected, and recovered. Immediately upon recovery the germ cell is transferred by pipette to a new petri dish containing a culture media used to dilute the transfer medium (HBSS) and begin the culturing of the germ cell. In this manner as many as 40 germ cells are collected in a petri dish from one female bee.

EXAMPLE 2

Preparation of Culture Medium

The culture medium in the petri dish receiving the germ cells is formulated in the following manner. A commercially available chemically defined basal medium such as SF-900 II SFM (Gibco) is supplemented with the following additives: 100 $\mu$g/ml fructose, 200 ng/ml insulin; 10 ng/ml leukemia inhibiting factor; and 10 ng/ml forskolin. The leukemia inhibitory factor represents a group of compounds commonly known as cytokines with known abilities to inhibit cell specialization through differentiation while not debilitating general cell growth. Other recognized cytokines includes stem cell factor. Forskolin represents a group of compounds commonly known as mitogens with known abilities to foster mitosis in cells and sometimes creating significant cell culture proliferation. Generally recognized other mitogenic agents include pokeweed and basic fibroblast growth factor. The pH of the medium is adjusted as needed to a value of 6.2. The culture temperature of the medium is 27° C. plus or minus one degree. All preparations are conducted in a manner so as to maintain the sterility of the culture medium containing both cytokinic and mitogenic agents together. The supplemented medium is designated the culture medium and the preferred embodiment but many variant formulations for culturing insect germ cells are contemplated.

EXAMPLE 3

Culture and Passage of Insecta Germ Cells

A first petri dish 100×15 mm sterilized plastic, kept in sterile condition, is prepared with 5 ml of culture medium. Pipetted germ cells from the HBSS dissection and wash are collected in this dish to dilute the transfer fluid and further decontaminate the germ cells. The dish is gently rocked to dilute and disperse the transfer fluid. This transfer is repeated twice more into newly prepared first dishes each time inspecting and deselecting germ cells for signs of damage or misidentification, each time the dilution and wash removes contamination possibilities. A second petri dish. 35×15 mm, sterilized plastic, is prepared with 3 ml of culture medium. From the first dish the germ cells are transferred by pipetting in such a manner as to widely disperse the individual cells to avoid early confluency. Both dishes are cultured at 27° C. without supplemental $CO_2$ and without stirring. A characteristic rosette formation around a single cell indicates mitotic activity. The medium is exchanged up to 80% by careful removal by pipette and replacement every 48 hours or more often depending on the degree of confluency and cell density. Contamination is removed at any time identified, as are any dead cells or group of cells. The cell culture is passaged at 50% colony confluency. Colony clusters dispersal is facilitated because the germ cells only loosely clump, are not attached to the plastic dish and tend to roll about the bottom of the dish once dispersed. Doubling time for the cells is typically 22 hours. Passages are into appropriately prepared larger volumes of culture medium in appropriately larger vessels. Sterile conditions are essential for culture survival, treatment by conventional methods of fungal and bacterial control are detrimental to insect germ cell culture. With proper care 20 doublings can be achieved. Arresting and storing the proliferation of the cultured germ cells is by means of conventional cryopreservation.

EXAMPLE 4

Cyropreservation of Insecta Germ Cells

While conditions for optimal germ cell survival in cryogenic storage varies with different species, the typical protocols include the following elements. From a passage of actively growing germ cells collect a sample in 2 ml of culture medium. Combine sample with 2 ml of culture medium with a concentration of 20% cryoprotective agent (typically glycerol or dimethyl sulphoxide). By pipette withdraw cell sample with 2 ml of culture medium and place in a appropriate freezing vial. Seal vial and place in a freezing tub to cool sample to $-80°$ C. at a consistent temperature drop over three hours. When the sample temperature has reached at least $-80°$ C. the vial is removed to storage in liquid nitrogen at $-196°$ C. Thawing to restore cell vitality is accomplished by placing frozen sample vial in a circulating water bath at 38° C. until sample reaches 27° C. whereby the germ cells substantially resume their status when originally collected.

While this preferred embodiment obtained germ cells from adult ovaries it is equally possible to secure them from other points in the insect life cycle. Germ cells can be obtained from the embryonic gonadal tubes of a pre-imago insect larva at an appropriate time of development, as well known in the art. Germ cell can also be obtained from an insect blastoderm before first cleavage, equally well known in the art Insecta germ cells in various forms of passage can be obtained from many sources, the difficult issues have always surrounded their in vitro culture.

Given the proliferation method herein disclosed it is understood that artificial genetic modification of one or more individual cells will permit replication of the specific successfully introduced trait or traits to all progeny of the modified germ cell. Techniques developed for gene manipulation of Drosophila are well known in the art and once similar gene maps are concluded for other insects the methodology is quite transferable.

Throughout this application various publications are referenced. The disclosures of these publications in their entireties are hereby incorporated by reference into this application in order to more fully describe the state of the art to which the invention pertains.

The foregoing examples are illustrative of the present invention, and are not to the constructed as limiting thereof. It will appear to those ordinarily skilled in the art that various modifications may be made to the disclosed embodiments, and that such modifications are intended to be within the scope of the present invention. The invention is defined by the following claims, with equivalents of the claims to be included therein.

What is claimed is:

1. A method of propagating undifferentiated Insecta germ cells in a sustained, feeder-cell independent culture comprising:

obtaining undifferentiated Insecta germ cells;

propagating said Insecta germ cells in a culture medium comprising a nutrient solution containing at least one soluble cytokine in an amount sufficient to inhibit Insecta germ cell differentiation and at least one soluble mitogen in an amount sufficient to stimulate multiple rounds of mitogenic division of said germ cells.

2. The method of claim 1, wherein said cytokine is leukemia inhibitory factor.

3. The method of claim 1, wherein said cytokine is stem cell factor.

4. The method of claim 1, wherein said mitogen is forskolin.

5. The method of claim 1, wherein said mitogen is basic fibroblast growth factor.

6. The method of claim 1, wherein said Insecta germ cells are of the order Hytmenoptera.

7. The method of claim 1, wherein said Insecta germ cells are of the species Osmia.

8. The method of claim 1, wherein said Insecta germ cells are of insects which pollinate entomophilous plants.

9. The method of claim 1, wherein said Insecta germ cells are obtained from the terminal filament area of the germinal zone of an ovariole of an insect.

10. The method of claim 1, wherein said Insecta germ cells are obtained from the embryonic gonadal tubes of a pre-imago insect.

11. The method of claim 1, wherein said Insecta germ cells are obtained from an insect blastoderm before first cleavage.

12. The method of claim 1, wherein at least one of said Insecta germ cells is genetically altered by genetic engineering means before said culturing.

* * * * *